(12) United States Patent
Lerch et al.

(10) Patent No.: US 8,212,220 B2
(45) Date of Patent: Jul. 3, 2012

(54) DUAL RADIATION DETECTOR

(75) Inventors: Michael Lloyd Franz Lerch, Bulli (AU); Anatoly Rozenfeld, Redfern (AU); Olexander Gektin, Kharkov (UA)

(73) Assignee: University of Wollongong, North Wollongong (GB)

( * ) Notice: Subject to any disclaimer, the term of this patent is extended or adjusted under 35 U.S.C. 154(b) by 164 days.

(21) Appl. No.: 12/526,100

(22) PCT Filed: Feb. 8, 2008

(86) PCT No.: PCT/AU2008/000159
§ 371 (c)(1),
(2), (4) Date: Oct. 8, 2009

(87) PCT Pub. No.: WO2008/095257
PCT Pub. Date: Aug. 14, 2008

(65) Prior Publication Data
US 2010/0090115 A1      Apr. 15, 2010

(30) Foreign Application Priority Data
Feb. 9, 2007   (AU) ............................... 2007900655

(51) Int. Cl.
*G01T 1/20*   (2006.01)
(52) U.S. Cl. .................... 250/370.11; 250/366
(58) Field of Classification Search .......... 250/370.11, 250/366
See application file for complete search history.

(56) References Cited

U.S. PATENT DOCUMENTS 3,539,806 A * 11/1970 Humphrey ................ 250/366
5,008,546 A *  4/1991 Mazziotta et al. ........ 250/366
5,180,916 A    1/1993 Lehtinen et al.

FOREIGN PATENT DOCUMENTS

JP         2001244494 A  *  9/2001

OTHER PUBLICATIONS

International Search Report; PCT/AU2008/000159; A. Walker; Apr. 11, 2008.

* cited by examiner

*Primary Examiner* — David Porta
*Assistant Examiner* — Hugh H Maupin
(74) *Attorney, Agent, or Firm* — Fish & Richardson P.C.

(57) ABSTRACT

A radiation detection apparatus and method, the apparatus (100) comprising a first scintillator (112) for interacting with radiation and outputting light in response thereto, a first photodetector (102) adjacent to the first scintillator (112) for receiving and detecting light from the first scintillator (112) and outputting (108) a first output signal in response thereto, a second scintillator (114) located around the first scintillator (112), for interacting with radiation and outputting light in response thereto, and a second photodetector (104) adjacent to the second scintillator (114) for receiving and detecting light from the second scintillator (114) and outputting (110) a second output signal in response thereto.

26 Claims, 7 Drawing Sheets

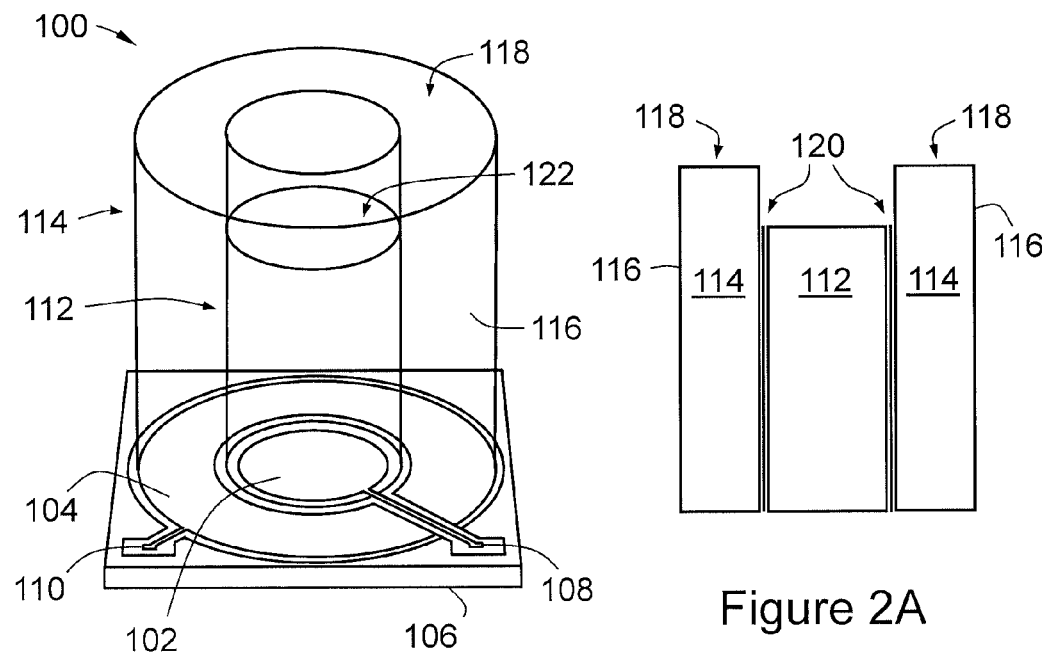
Figure 1
Figure 2A
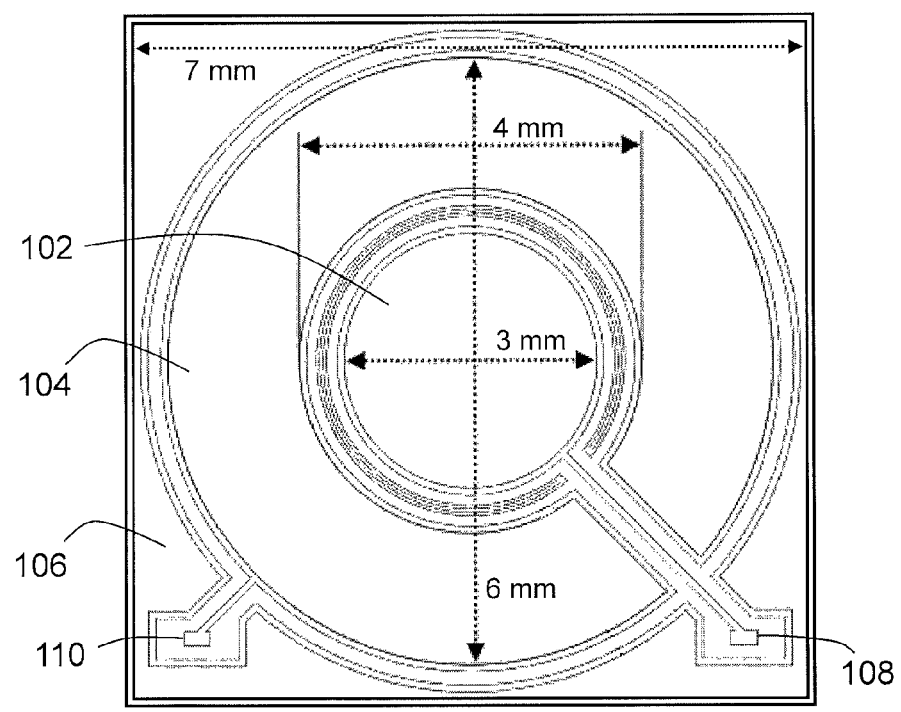
Figure 2B

DUAL RADIATION DETECTOR

RELATED APPLICATION

This application is based on and claims the benefit of the filing date of AU application no. 2007900655 filed 9 Feb. 2007, the content of which as filed is incorporated herein by reference in its entirety.

FIELD OF THE INVENTION

The present invention relates most particularly to a radiation detector with dual photodetectors and either a single or dual scintillators, and to a radiation probe based on such a detector.

BACKGROUND OF THE INVENTION

In the surgical treatment of cancer, and particularly in the treatment of breast cancer, the extend of intervention (e.g. mastectomy or 'lumpectomy') constitutes an important decision. The status of the lymph nodes—ascertained by biopsy during surgery—is a particularly important factor in the making of that decision. The sentinel lymph node (SN) is an important indicator of the spreading of the cancer cells from the primary tumour through the lymphatic system. To localize the SN with high accuracy intra-operatively, the radio guided technique is typically employed: a radioactive tracer based on Tc-99m (with a 141 keV gamma emission) is administered in the tumour, and appears—via the lymphatic drain—in the SN shortly thereafter. Locating the SN can be done intra-operatively with gamma probes in spectroscopy mode for identifying the gamma isotope.

Different types of gamma probes have been developed based on scintillator detectors and solid sate semiconductor detectors. These include probes based on a single CsI(Tl) or NaI(Tl) scintillator optically coupled to photomultipliers by fibre optics guides, and scintillators directly coupled to single photodiode silicon detectors (J. Chavanelle and M. Parmentier, "A CsI(Tl)-PIN photodiode gamma-ray probe," Nucl. Instr. & Meth., 504 (2003) 321-324). This technology is used to localize small tumours during surgery or in conjunction with endoscopic examination.

Single scintillator gamma probes with a passive collimator (of Pb or Tungsten) are used to improve localization of deeply located radioactivity. This may be required owing to attenuation of scattered radiation or gamma photons from background radiation due to activity uptake in organs other than the tumour. Such gamma probes require high Z detector material (e.g. scintillator or CZT), and a detector module operating in a spectroscopy mode both so that energy windows suitable for the particular isotope can be selected and so that gamma photons from the isotope can better be discriminated from other radiation scattered in the patient's body. Such an approach is suitable for gamma sources with photon energies less then 200 keV. Localization of radioactive sources with high gamma energies—such as PET isotopes (511 keV)— using passive collimation is impractical owing to the thick collimator wall of such probes, which make the probes too bulky for many intraoperative applications.

Another approach, proposed by H. Watabe et al. ("Development of a miniature gamma-ray endoscopic probe for tumour localization in nuclear medicine," IEEE Trans. on Nucl. Sci. 40 (1993) 88-94), attempts to improve spatial resolution of source localization in cases of gamma photons with energy greater than 200 keV. This approach employs dual BGO ($B_4Ge_3O_{12}$) scintillators closely coupled to each other but without a collimator, each of the two scintillators being connected with a fibre optic light pipe to its own photomultiplier. The random coincidence technique is then used, on the basis that the probability of a random coincidence of events in the two scintillators is P1×P2, where P1 and P2 are the probabilities of gamma photon registration by the first and second detectors respectively. It is clear that, for localized activity, the number of random coincidence events decreases more rapidly with distance than the number of events for a single detector, and this effect can potentially be used to achieve better spatial resolution. The disadvantage of this approach— whether using a single or dual scintillator detectors—is that photopeak resolution deteriorates owing to the coupling of the fibre optic light pipe and the photomultiplier. This is due to loss of photons and hence deterioration in the spatial resolution of the probe.

The use of two concentric collimated scintillator detectors coupled by light pipes to two photomultiplier has been proposed by T. S. Hickernell et al. ("Dual-Detector probe for Surgical tumour staging", J. Nucl. Med 29 (1988) 1101- 1106), where the outer detector suppresses background gamma activity. However, this probe has limitations for large tumours determinations, in addition to the aforementioned disadvantages in the coupling of scintillators to photomultipliers with light pipes.

PET isotopes (i.e. mixed field beta and 511 keV gamma field) or pure beta isotopes (e.g. P-32) for labelling cancer cells improves localization of activity (and hence of the tumour) owing to their short range compared to gamma radiation. However, gamma background activity from other parts of the body remains a problem for the accurate detection of beta particles on a gamma background.

U.S. Pat. No. 5,008,546 proposes a beta probe with improved selectivity in a mixed gamma-beta field. This probe employs two closely coupled plastic scintillators, or concentric scintillators where the outer scintillator is protected from beta radiation by shielding (e.g. 1 mm thick stainless steel). The plastic scintillators are optically coupled by fibre optics bundles to respective photomultipliers. Photomultipliers employ high bias voltages (of the order of 1000 V) and are separated from their corresponding scintillators. Radiative counts produced by pure beta radiation in an unshielded plastic scintillator are obtained by weighted subtraction of the count from the second plastic scintillator.

Low Z scintillators have the advantage when used in detector modules for beta detection of having low efficiency for the detection of high energy gamma radiation. However, they do not allow such probes to be used as efficient gamma probes in spectroscopy mode.

R. R. Raylman and A. Hyder ("A dual surface barrier detector unit for beta-sensitive endoscopic probes", IEEE Trans on Nucl. Sci., 51 (2004) 117-121) report the use of dual detectors for beta detection in a high energy gamma background of a PET (FDG, that is, F-18) isotope for an endoscopic probe based on two miniature 3 mm diameter Si surface barrier detectors mounted back to back. Gamma background can be subtracted from the front detector by weighted count output of the back detector. While the detector module is small, the disadvantages of such a probe arise from the complicated mounting of detector and read out electronics and its inutility as a gamma spectroscopy intraoperative probe for high energy gamma isotopes, such as Tc-99m.

The identification of the signature of radioactive isotopes with medium and low energy gamma photons can be difficult in the presence of high energy masking gamma isotopes, as the monitored events may be statistically poor compared with the Compton scattering background from higher energy masking isotopes. This problem has been addressed with the nuclear spectroscopy technique of anti-Compton spectrometry, in which events from a primary detector are rejected if associated with interactions via the Compton scattering process. Such events produce no usable signal for spectroscopy purposes.

The rejection is achieved by surrounding the primary detector with an active Compton shield, which detects the Compton scattered photons originating from within the primary detector thereby producing a veto signal for the primary detector data acquisition system. This results in the suppression of the Compton continuum in the primary detector spectrum and hence to a greater probability of detection of lower energy gamma photons otherwise statistically lost in the Compton background. It also allows the use of smaller primary spectroscopy grade detectors while maintaining a good photopeak-to-compton (P/C) ratio for a wide range of photon energies.

R. Aryaeinejad et al. ("High resolution Compton-suppressed CZT and LaCl3 detectors for fission identification," IEEE Trans on Nucl. Sci., 52(5) (2005) 1728-1732) propose an anti-Compton spectrometer for the detection of fissile materials using a 10×10×5 $mm^3$ CZT primary detector and a NaI(Tl) or BGO veto detector. The primary and veto detectors thus operate on different principles, the former being semiconductor based, the latter scintillator based. This is inconvenient, requiring both photomultipliers and solid state detector readout electronics as well as different high voltage biasing circuitry. It also leads to a large volume of inactive material, a so-called "dead layer," between the primary and veto detectors that reduces Compton suppression efficiency. One proposal to alleviate this problem involves connecting the CZT primary detector to a preamplifier located externally to the veto detector, but this degrades the main advantage of CZT, namely, high energy resolution (reported to be 4.6% for 661.7 keV).

U.S. Pat. No. 6,710,349 discloses a detector with a position sensitive radiation detector having a radiation sensitive area and a radiation insensitive area, a first scintillator adjacent to the radiation sensitive area and a second scintillator adjacent to the second radiation insensitive area. The second scintillator is optically coupled to the first scintillator, and the decay times of the first and second scintillators are different.

SUMMARY OF THE INVENTION

According to a first broad aspect, the present invention provides a radiation detection apparatus, comprising:
- a first scintillator for interacting with radiation and outputting light in response thereto;
- a first photodetector adjacent to the first scintillator for receiving and detecting light from the first scintillator and outputting a first output signal in response thereto;
- a second scintillator located around the first scintillator, for interacting with radiation and outputting light in response thereto; and
- a second photodetector adjacent to the second scintillator for receiving and detecting light from the second scintillator and outputting a second output signal in response thereto.

The first and second scintillators are preferably directly optically coupled to the first and second photodetectors respectively.

Thus, because the scintillators are adjacent to their respective photodetectors (that is, without light pipe or other interconnecting means), it is unnecessary to employ any mediating light guide, and the apparatus can be made particularly compact and efficient. The output of the first photodetector can be used as the principal output channel of the apparatus; the output of the second photodetector can be used to gate the principal output (as is explained below) or, if resolution is less important, to increase total efficiency.

The scintillators are preferably of high Z material. Preferably the second scintillator extends away from the first and second photodetectors beyond the first scintillator.

In one embodiment the apparatus includes an optical isolator located between the first and second scintillators. Such an isolator may not block all optical photons, but it nonetheless reduces the noise from various sources from being included in the output of the first photodetector.

In a particular embodiment the first and second scintillators are cylindrical and coaxial.

In one embodiment the first and second photodetectors are photodiodes.

Preferably the first and second photodetectors are coplanar and concentric. This arrangement allows the apparatus to be especially compact.

Preferably the first and second photodetectors are on a single substrate (typically a Si wafer substrate).

In a particular embodiment, the apparatus includes anticoincidence electronics arranged to receive the first output signal from the first photodetector and the second output signal from the second photodetector, and to output a signal corresponding to the first output signal when the first output signal is not in coincidence with the second output signal.

Thus, events corresponding to the scattering of gamma or other radiation from one scintillator to the other will produce coincident output signals, but are excluded from the first output signal to improve spatial resolution In some embodiments, the apparatus additionally comprises one or more further scintillators with corresponding photodetectors.

In some embodiments, the apparatus is adapted to act as a beta detection apparatus.

In one embodiment, the apparatus includes shielding (such as thin metal shielding) located around exposed portions of the second scintillator to prevent beta particles from interacting with the second scintillator. This embodiment allows beta particles to interact with the first scintillator and hence be detected; any gamma or X-ray background detected via interaction with the first scintillator can be subtracted according to the level of gamma or X-ray background events detected via the second scintillator, which is particularly useful in high gamma or X-ray background environments.

According to a second broad aspect, the present invention provides a radiation detection apparatus, comprising:
- a scintillator for interacting with nuclear or X-ray radiation and outputting light in response thereto;
- a first photodetector adjacent to the scintillator for receiving and detecting radiation and outputting a first signal in response thereto;
- an optical barrier between the scintillator and the first photodetector that is substantially opaque to optical and near optical wavelength radiation but transparent to photons or electrons scattered from the first photodetector; and
- a second photodetector adjacent to the scintillator and to the first photodetector for receiving and detecting light from the scintillator and outputting a second signal in response thereto.

This aspect is principally intended to be used with the first and second photodetectors directed generally towards the radiation source of interest and the scintillator away, so that the first photodetector directly detects the nuclear or X-ray radiation, and the second photodetector can be used either to augment the total detection efficiency or for coincidence or anticoincidence measurements.

The invention also provides methods for measuring or monitoring radiation employing any of the apparatuses described above.

Thus, in another broad aspect, the invention provides a method of measuring or monitoring radiation, comprising:
receiving radiation with a first scintillator;
detecting light output by the first scintillator with a first photodetector located adjacent to the first scintillator;
outputting a first output signal from the first photodetector in response to light detected by the first photodetector;
receiving radiation with a second scintillator located around the first scintillator;
detecting light output by the second scintillator with a second photodetector located adjacent to the second scintillator; and
outputting a second output signal from the second photodetector in response to light detected by the second photodetector.

The method may include directly optically coupling the first and second scintillators to the first and second photodetectors respectively.

The method may include generating a principal output comprising or derived from the first output signal, and either gating the principal output with the second output signal or increasing total detection efficiency with the second output signal.

The method may include optically isolating the first and second scintillators.

In another broad aspect, the invention provides a method of measuring or monitoring radiation, comprising:
receiving nuclear or X-ray radiation with a scintillator;
receiving and detecting radiation with a first photodetector located adjacent to the scintillator and arranged to output a first signal in response to detected radiation;
locating an optical barrier between the scintillator and the first photodetector that is substantially opaque to optical and near optical wavelength radiation but transparent to photons or electrons scattered from the first photodetector; and
receiving and detecting radiation from the scintillator with a second photodetector located adjacent to the scintillator and to the first photodetector, the second photodetector being arranged to output a second signal in response to detected radiation.

The invention also provides a probe comprising any of the apparatuses described above. In one embodiment, for example, the invention provides an intraoperative probe for use during surgery.

The above aspects can be variously employed, for example, as a gamma-beta probe for radio guided surgery for the precise location of radiolabeled malignant tissue, for gamma-beta (PET) or dual gamma isotopes (for example PET+Tc 99), as a gamma probe, as a beta probe in a gamma background, or as a probe for the detection of lower energy gamma/X-ray isotopes in a masking high energy gamma background (for safeguard and security applications).

BRIEF DESCRIPTION OF THE DRAWING

In order that the invention may be more clearly ascertained, embodiments will now be described, by way of example, with reference to the accompanying drawing, in which:

FIG. 1 is a schematic view of a detector module according to an embodiment of the present invention;

FIG. 2A is a schematic cross sectional view of the inner and outer scintillators of the detector module of FIG. 1;

FIG. 2B is a plan view of the inner and outer photodiodes and Si base of the detector module of FIG. 1;

DETAILED DESCRIPTION

Figure 3A:
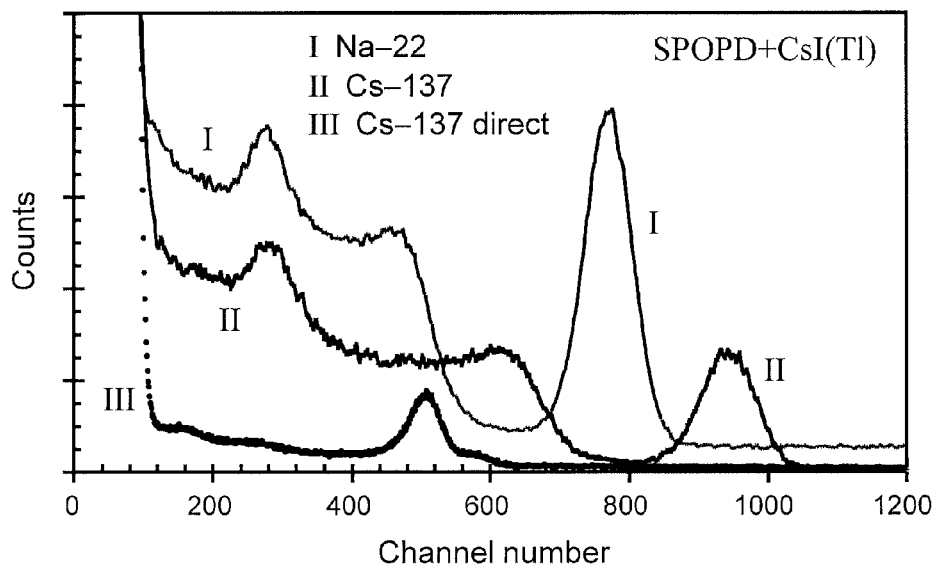
FIG. 3A plots energy spectra collected with the detector module of FIG. 1 with a CsI(Tl) inner scintillator, with a Na-22 source and a Cs-137 source, and an energy spectrum collected with the detector module of FIG. 1 without its inner scintillator, with a Cs-137 source, for comparison purposes.
Figure 3B:
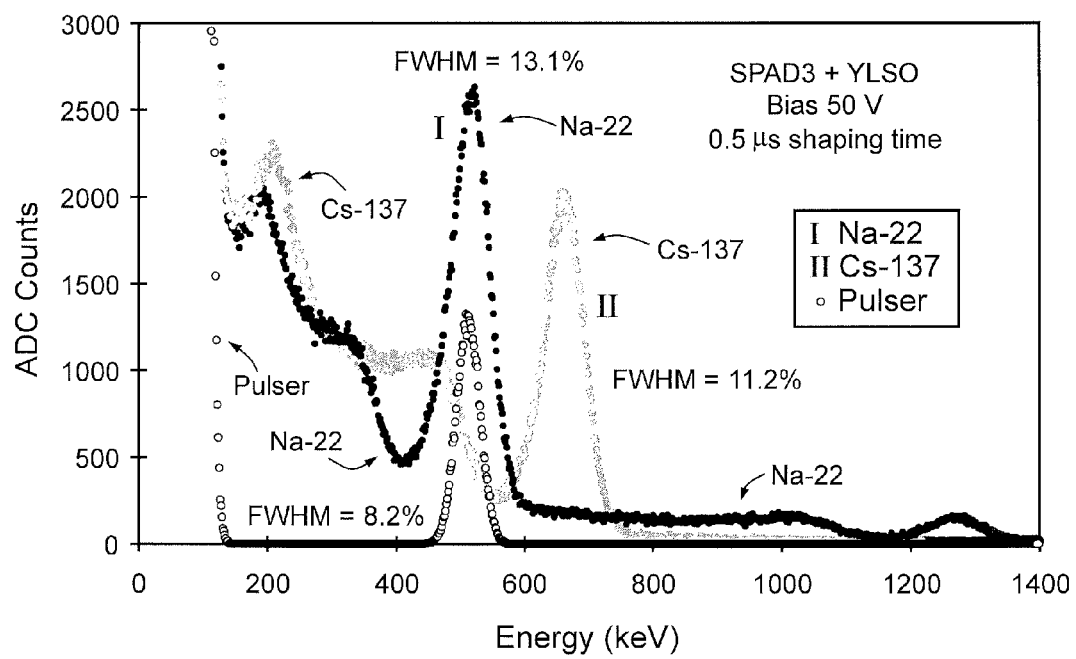
FIG. 3B plots energy spectra collected with the detector module of FIG. 1 with a YLSO inner scintillator with Na-22 and Cs-137 sources, compared with a pulser.

FIG. 1 is a perspective, schematic view of a detector module 100 comprising dual concentric Si planar photodiodes on a single Si wafer directly optically coupled to dual optically isolated high Z scintillators, and so referred to below as Dual Photodiode Dual Scintillator (DPDS) detector module 100. Thus, referring to FIG. 1, DPDS detector module 100 comprises a generally circular, inner Si planar photodiode 102 and a generally annular, outer Si planar photodiode 104 (both p-n junctions are P+ doped), located concentrically upon an N+ doped Si wafer substrate or base 106. Photodiodes 102, 104 are in fact produced on the Si base 106, which makes them particularly convenient to manufacture, especially in compact form. The photodiodes 102, 104 are of approximately 0.5 mm thickness, and have respective contact pads 108, 110. Above the photodiodes 102, 104 (hence opposite base 106) and directly coupled thereto are two corresponding high Z scintillators: inner scintillator 112 and outer scintillator 114. It should be noted that the shape of DPDS detector module 100 may be varied, according to application or manufacturing convenience, though its cross section will generally be of regular form. For example, outer scintillator 114 has—in some embodiments—a square cross section, with outer photodiode 104 being correspondingly square.

Scintillators 112, 114 have respective cross sections that conform to photodiodes 102, 104, respectively, so that events in scintillators 112, 114 have the greatest probability of being detected by photodiodes 102, 104 respectively. FIG. 2A is a schematic cross sectional view of scintillators 112, 114: as is apparent from this figure, both extend vertically but inner scintillator 112 is not as long (or tall in this view) as outer scintillators 114.

FIG. 2B is a plan view of the inner and outer photodiodes 102, 104 and base 106. Typical dimensions are indicated: the base is 7 mm square, inner photodiode 102 (and hence inner scintillator 112) has a diameter of 3 mm, and outer photodiode 104 (and hence outer scintillator 114) has an inner diameter of 4 mm and an outer diameter of 6 mm. However, as will be appreciated by those in the art, a great range of sizes can be employed according to intended application.

Inner and outer scintillators 112, 114 are separated optically by an optical isolator in the form of a cylinder of tetrapack paper 120 with 99% light reflection located between the scintillators 112, 114. Otherwise exposed surfaces of inner and outer scintillators 112, 114 are covered with reflective paint (not shown), to (internally) reflect photons of optical wavelengths so that these photons do not escape from the scintillators without being detected by the photodiodes 102, 104. These surfaces are hence the external and end faces 116, 118 of outer scintillator 114, and the end face 122 of inner scintillator 112.

Contact pads 108, 110 of inner and outer photodiodes 102, 104 respectively are directly connected to miniature preamplifiers (not shown), preferably attached to the rear of a mount (not shown) of DPDS detector module 100.

DPDS detector module 100 is intended to be oriented in use with scintillators 112, 114 directed towards the source of the radiation (though in some applications other orientations may be acceptable and indeed preferred). In use, outer scintillator 114 performs two principal roles. Firstly, it shields inner scintillator 112 from gamma or X-ray photons that would otherwise contribute to background counts. Secondly, outer scintillator 114 allows the user to discriminate against photons that have been highly Compton scattered in the medium surrounding the source of interest, laterally into the detector module 100. Such photons will commonly pass through outer scintillator 114 before reaching inner scintillator 112, so can be excluded from the ultimate output by rejecting any events detected by inner photodiode 102 in coincidence with an event detected by outer photodiode 104. The final output of the detector module 100 is thus usually drawn exclusively from inner photodiode 102 (or "channel 1", drawn from contact pad 108), though—in lower applications where lower resolutions are acceptable—the output of outer photodiode 104 (or "channel 2", drawn from contact pad 110) may also be used to increase the detector modules efficiency as a gamma probe.

Owing to the direct coupling of the respective scintillators 112, 114 and photodiodes 102, 104, DPDS detector module 100 does not require optical pipes to transmit light from the former to the latter, and do not require photomultipliers employing high bias voltages. This arrangements provides high light collection and improved energy resolution compared with many previous designs that employ light pipes.

DPDS detector module 100 can also act as a beta probe, such as in intraoperative surgical applications in a high energy gamma background environment (for example with PET isotope) by shielding the external and end faces 116, 118 of outer scintillator 114 from beta interaction, such as with thin metal shielding. The output of outer photodiode 104, suitably normalized, is subtracted from the output of the inner photodiode 102, to provide a measure of the counts attributable to beta particles collected by the an inner photodiode 102. No metal shielding is required between inner and outer scintillators 112, 114 owing to the high stopping power for beta particles of high Z scintillators (e.g. CsI(Tl) or YLSO). Furthermore, DPDS detector module 100, in contrast to other probes with PD-CsI(Tl) or photomultiplier-single scintillator, does not require a tungsten or lead collimator. Outer high Z scintillator 114 acts as a collimator for inner scintillator 112 in gamma spectroscopy mode. Thus, DPDS detector module 100 can be used both as a beta and as a gamma probe, simultaneously if desired.

DPDS detector module 100 may be used in medical applications as an intraoperative surgical probe. In such applications, scintillators 112, 114 are advantageously CsI(Tl) (Z=50) or YLSO (Z=55) (fast YLSO scintillators being particular suitable for high speed detection performance for high activities measurements). This provides high efficiency gamma detection for photon energies in the range 80-662 keV, which are of interest for nuclear medicine. Additionally, this configuration provides, when the detection electronics are used in spectroscopy mode, good energy resolution for 140.5 keV (Tc-99m) and 511 keV (PET FDG) labelled isotopes.

FIG. 3A plots energy spectra collected with DPDS detector module 100 (with a CsI(Tl) inner scintillator 112) from: I) the $\beta^+$ emitter Na-22 ($\gamma$=511 keV), and II) Cs-137 ($\gamma$=661.7 keV). The data were collected from the first channel (i.e. inner scintillator 112) only. For comparative purposes, data collected from the direct interaction of Cs-137 low energy photons (y=35 keV) with Si inner photodiode 102 (i.e. without inner scintillator 112 in place) were also collected and plotted in this figure (data points III). FIG. 38 plots energy spectra collected with DPDS detector module 100 (with a YLSO inner scintillator 112) from: I) Na-22 (511 keV), and II) Cs-137 (661.7 keV), compared with a pulser (open data points), to demonstrate the low noise electronics noise. The data were collected from the first channel (i.e. inner scintillator 112) only. The operating bias was 20 V (cf. the typical 1000 V required a photomultiplier).

With a CsI(Tl) inner scintillator 112 and inner photodetector 102, energy resolution was 5% for 661.7 keV gamma photons, 6% for 511 keV gamma photons and 25% for 122.1 keV (from Co-57) gamma photons. This is substantially better than the typical figures obtained with a photomultiplier directly coupled to a NaI(Tl) scintillator.

Figure 4:
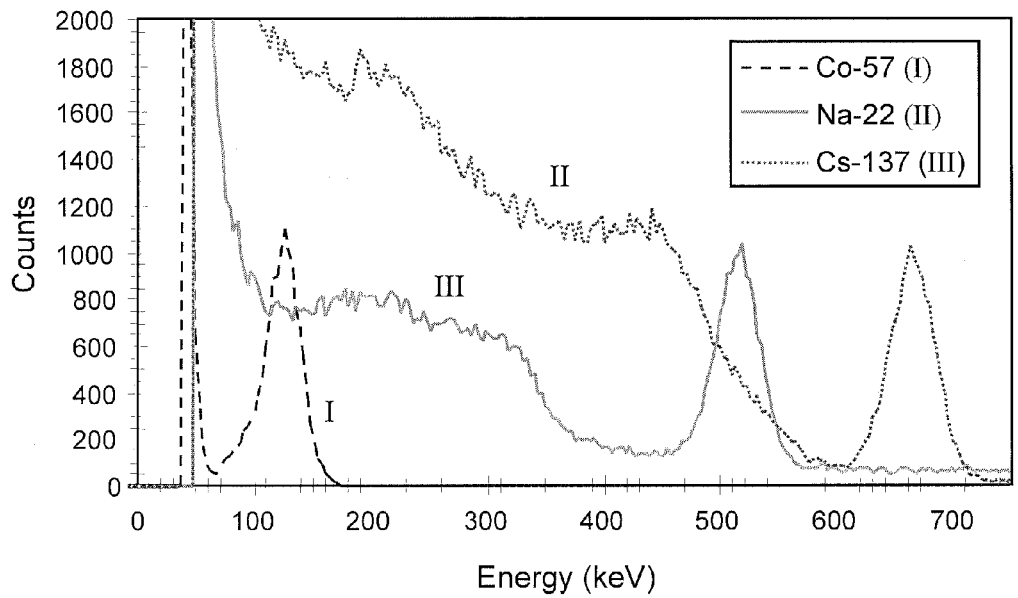
FIG. 4 shows the spectroscopy performance of the detector module of FIG. 1 with Co-57 (122.1 keV), Na-22 (511 keV) and Cs-137 (661.7 keV)

FIG. 4 shows the spectroscopy performance of DPDS detector module 100, with data extracted only from inner photodiode 102. Inner photodiode and scintillator 102, 112 had diameters of 3 mm, and the outer diameter of outer photodiode and scintillator 104, 114 was 6 mm. Data points I (dashed curve) are from Co-57 (122.1 keV), data points II (solid curve) are from Na-22 (511 keV), and data points III (dotted curve) are from Cs-137 (661.7 keV). These plots demonstrate the module's performance in resolving isotopes with gamma energies as low as 122.1 keV, below the activity of Tc-99m (140 keV).

Figure 5:
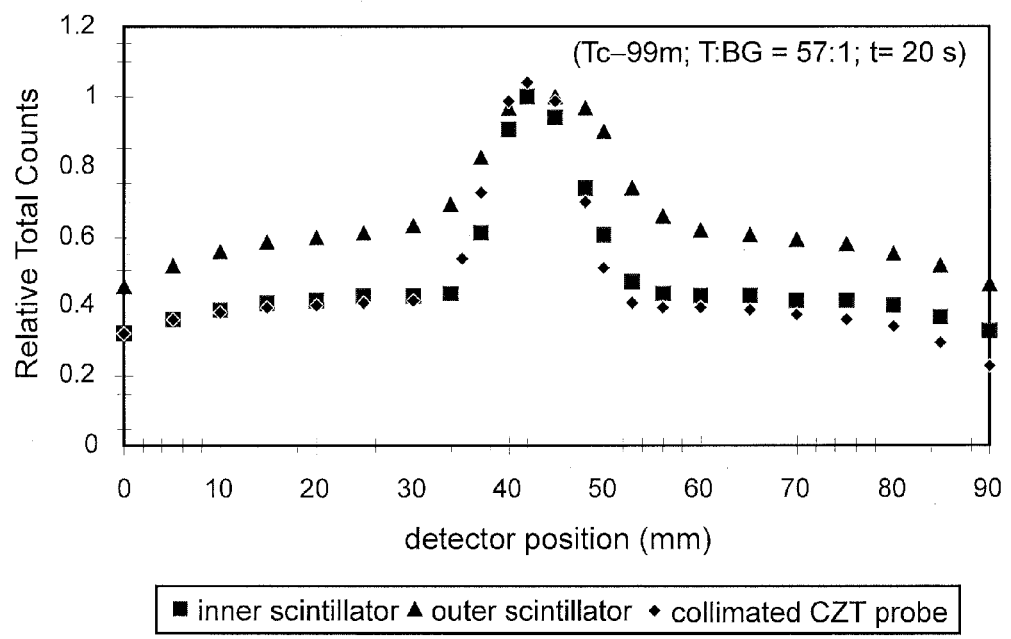
FIG. 5 is a plot of data collected with the detector module of FIG. 1 scanned across a Tc-99m source ("tumour") located on the surface of the water phantom providing a uniform background activity, providing a measure of the normalized spatial resolution of the detector module of FIG. 1, and comparable data collected with a CZT collimated probe for comparison purposes.
Figure 6:
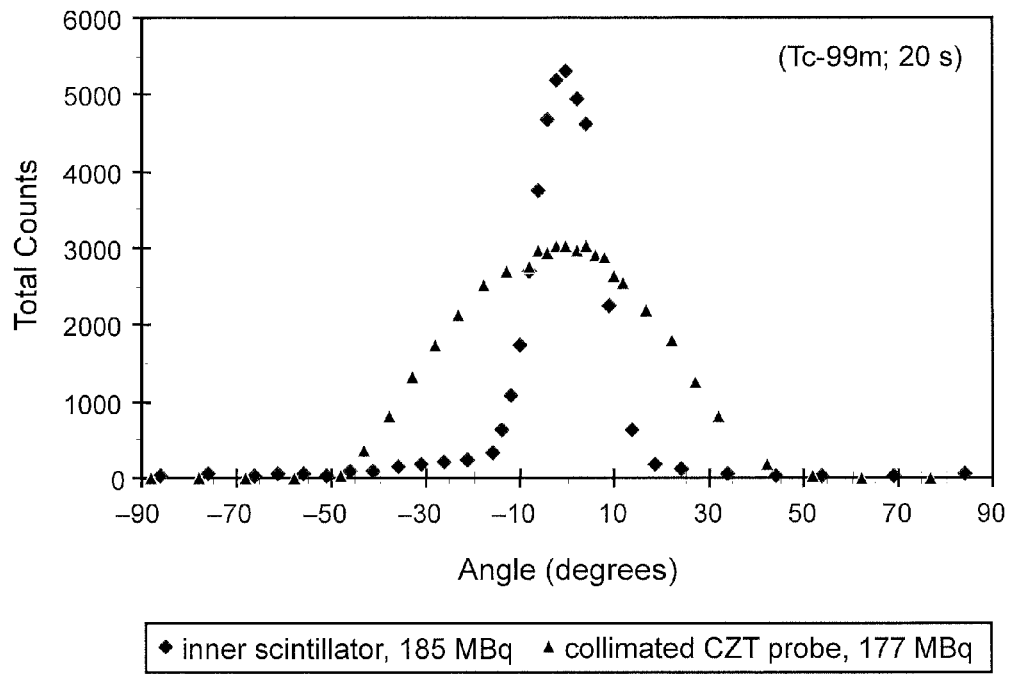
FIG. 6 is a plot of data from the detector module of FIG. 1 for a Tc-99m source at a distance of 4 cm compared with data from a CZT collimated probe, as measure of angular resolution.

FIGS. 5 and 6 are the results of measurement performed to demonstrate the resolution of an intraoperative DPDS detector module 100 according to this embodiment, without tungsten collimator and operating in gamma spectroscopy mode for Tc-99m, in comparison with a commercially available tungsten collimated CZT detector based probe.

FIG. 5 is a plot of data obtained with DPDS detector module 100 from a "tumour" (modelled with a 3 mm Tc-99m source at a depth of 1 cm in a water phantom with a uniform Tc-99m activity) on a Tc-99m radiation background (provided by the uniform Tc-99m activity of the water phantom), to test the spatial resolution of the detector module 100. The DPDS detector module 100 was scanned above the water phantom for a collection time of 20 s. The "tumour" to background activity ratio (T:BG) was 57:1. The results from the inner scintillator 112 and the outer scintillator 114 are plotted separately, and compared with data collected under comparable conditions with the collimated CZT probe. The data have been normalized. It can be seen from this figure that DPDS detector module 100 has a similar spatial resolution to the CZT collimated probe, particularly in the case of the inner scintillator 112.

FIG. 6 is a plot of data from DPDS detector module 100 for a Tc-99m source in air at a distance of 4 cm from the DPDS detector module, and—for comparison—from the CZT collimated probe, as an indication of the angular resolution of both detectors. Collection time was 20 s in both cases. DPDS detector module 100 demonstrates substantially better angular resolution in air than the CZT collimated probe.

DPDS detector module 100 may also form the basis of an anti-Compton spectrometer, which may be of suitable size to be hand-held such as used to identify radioactive isotopes for security purposes. DPDS detector 100 has several characteristics that make it advantageous for anti-Compton spectrometry: 1) the same type of detector is used in both the primary and veto channels, hence simplifying readout electronics and reducing size; 2) the absence of photomultipliers, so a high voltage bias is not required (photodiodes 102, 104 typically being biased with ~25 V); 3) no "dead layer" between detectors that would attenuate low energy gamma photons and reduce Compton suppression; 4) readout preamplifiers can be attached directly to the back of the base 106 of photodiodes 102, 104, minimizing noise due to logistical requirements. Optionally, the outer diameter of outer photodiode 104 can be increased to increase the probability of detection of the scattered Compton photons.

Figure 7:
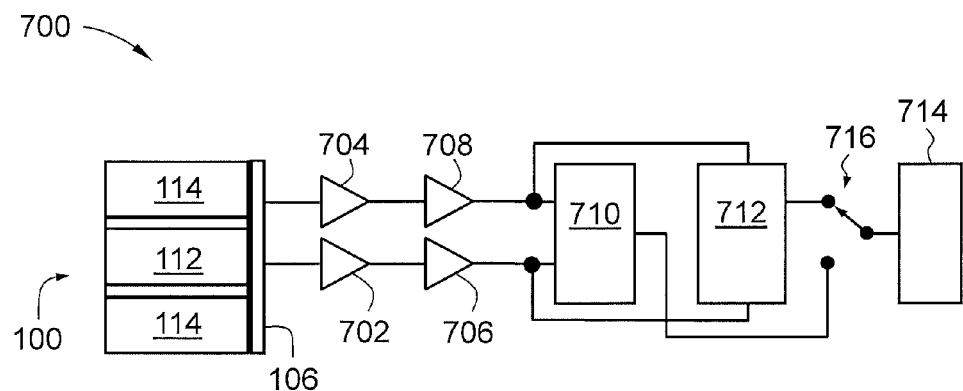
FIG. 7 is a schematic diagram of an anti-Compton spectrometer according to an embodiment of the present invention, based on the detector module of FIG. 1.

FIG. 7 is a schematic diagram of an anti-Compton spectrometer 700 according to an embodiment of the present invention, based on DPDS detector module 100. Spectrometer 700 includes a DPDS detector module 100, first and second preamplifiers 702, 704 and first and second amplifiers 706, 708, for the outputs of inner and outer photodiodes 102, 104 respectively. Spectrometer 700 also includes an anticoincidence/coincidence unit 710 and a summing unit 712, into both of which the outputs of the first and second amplifiers 706, 708 are fed, and a counter 714 (typically an MCA). Spectrometer 700 further includes a switch 716 for selectively directing the output of either the anticoincidence/coincidence unit 710 or the summing unit 712 into counter 714.

Spectrometer 700 has two modes. The first—when the output of the summing unit 712 is collected (as depicted in this figure)—provides a preliminary survey for the identification of the isotope; maximum detection efficiency is employed, with both scintillators 112, 114 operating in parallel. The second or anti-Compton mode employs the output of the anticoincidence/coincidence unit 710 counter, so that Compton background is suppressed. This operates by rejecting events that are detected in inner photodiode 102 if in coincidence with an event detected in outer photodiode 104, such coincidence events being commonly attributable to photons Compton scattered around the source of interest into outer scintillator 114, and then into inner scintillator 112.

Figure 8:
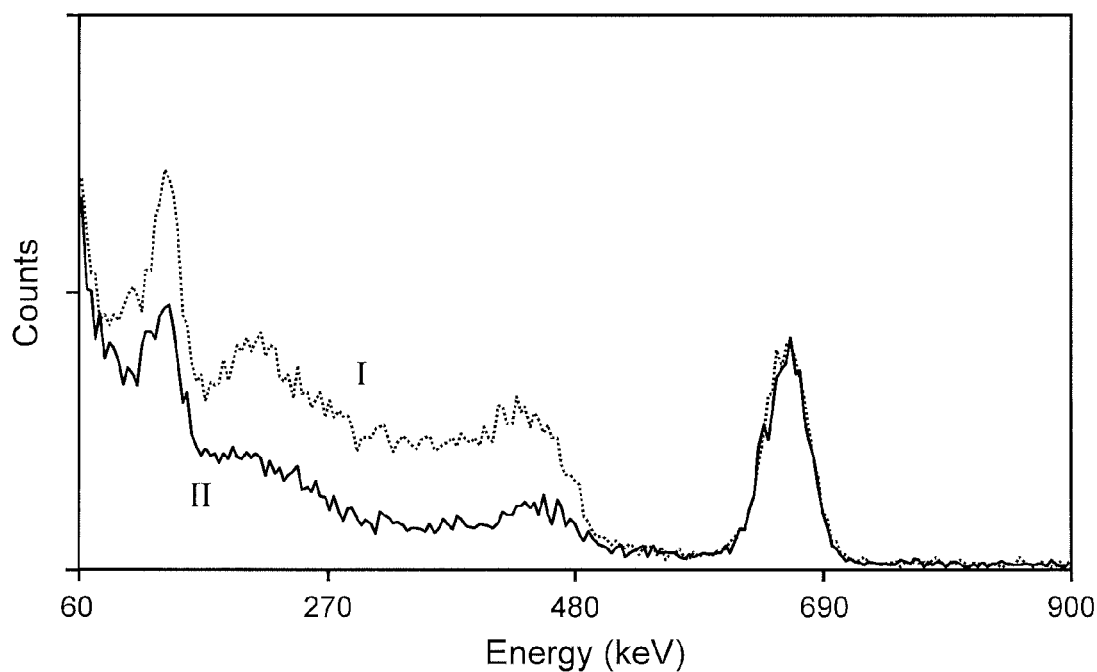
FIG. 8 is a plot of two data sets collected with the spectrometer of FIG. 7 from a Co-57 source, without Compton suppression and with Compton suppression for masking Cs-137.

FIG. 8 is a plot of two data sets collected with spectrometer 700 from a Co-57 source (122.1 key), I) without Compton suppression (dashed curve), and II) with Compton suppression for masking Cs-137 (solid curve). The diameter of inner photodiode 102 and scintillator 112 of spectrometer 700 was 3 mm; inner scintillator 112 had a height of 3 mm. Rather than generally cylindrical, outer scintillator 114 was generally cubic with outer dimensions $10 \times 10 \times 10$ mm$^3$; hence, outer photodiode 104 was essentially square and of $10 \times 10$ mm$^2$. Substantial Compton suppression is apparent in the Compton suppressed data set (II).

Figure 9:
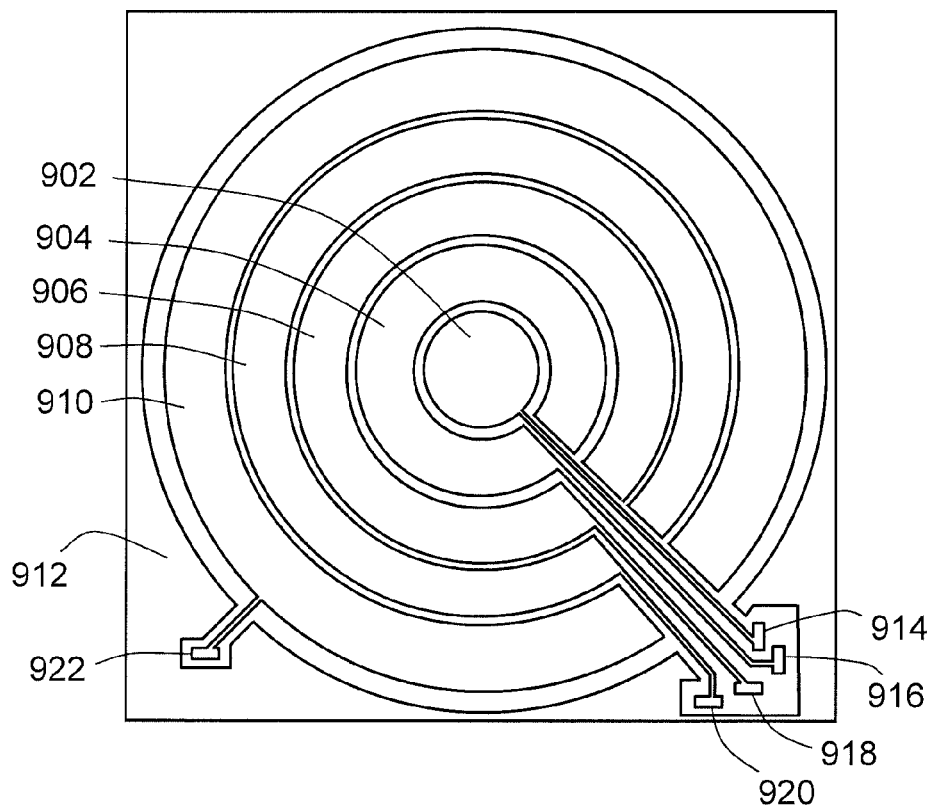
FIG. 9 is a plan view comparable to FIG. 2B of the inner photodiode, outer photodiodes and Si base of a pixelated detector module according to an embodiment of the present invention.

Particularly in spectrometer 700, but also in other embodiments, outer photodiode 104 may be divided (or 'pixelated') into a plurality of concentric detector elements to decrease the capacitance of any one detector element and hence the associated noise of the electronics. Ideally such embodiments also have corresponding pixelated, optically coupled scintillators elements. In such embodiments, any pixel can be considered as an inner detector with all surrounding pixels outer detectors. This configuration improves the energy resolution of photons detected in each pixel. FIG. 9 is a plan view—comparable to that of FIG. 2B—of the inner photodiode 902, respective outer photodiodes 904, 906, 908 and 910 and base 912 of such a pixelated detector module otherwise comparable to detector module 100 of FIG. 1. Inner and outer photodiodes 902, 904, 906, 908 and 910 have respective contact pads 914, 916, 918, 920 and 922. The diameter of inner photodiode 902 is comparable to that of inner photodiode 102 of DPDS detector module 100; the embodiment shown in FIG. 900 is thus larger in overall diameter than that of DPDS detector module 100 of FIGS. 1 to 2B. In other embodiments, however, outer photodiodes 904, 906, 908 and 910 may collectively have a total outer diameter comparable to that of outer photodiode 104 of DPDS detector module 100.

Another application of DPDS detector module 100 is in the detection of low energy gamma photons of energy 20-100 keV in a strong masking Cs-137 radiation field, such as in area of radioactive material safeguards and security. For example, the International Atomic Energy Agency (IAEA) are required to check for such radiation in situ when verifying the state of spent fuel assemblies stored under water on stacked trays. Spent fuel can be identified by detecting uranium fluorescent emission, principally in the energy range 95-110 keV (induced by the strong 661.7 keV Cs-137 background due to burnt fuel). To improve the low energy response, an anti-Compton spectrometer according to another embodiment of the present invention is provided, in the form of a portable low energy gamma/X-ray probe for safeguard and other applications where low energy X-ray photons must be monitored against an intense high energy photons gamma background.

Silicon detectors with a sensitive volume thickness of 0.4-0.5 mm have reasonable efficiency for 10-100 key gamma photons and excellent energy resolution. However, a strong high energy photon background from 661.7 keV gamma photons deposits energy in Si detectors of 0.4-0.5 mm thickness of up to 500 keV, which makes the observation of low energy X-ray events difficult or impossible.

Figure 10:
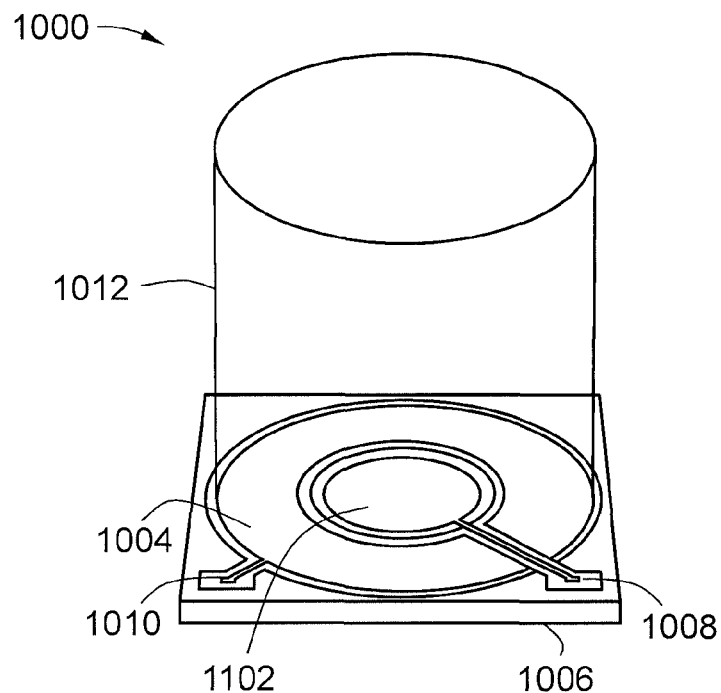
FIG. 10 is a perspective view of a single scintillator detector module according to another embodiment of the present invention.

Thus, according to the present invention there is provided a Dual Photodiode Singe Scintillator (DPSS) detector module, shown generally at 1000 in FIG. 10. DPSS detector module 1000 utilizes the same dual Si photodiode structure as does DPDS detector module 100 (see, in particular FIG. 2B), but only a single scintillator adjacent to both photodiodes. Hence, FIG. 10 is a perspective view of DPSS detector module 1000, which comprises a generally circular, inner Si planar photodiode 1002 and a generally annular, outer Si planar photodiode 1004 (both p-n junctions P+ doped), located concentrically upon an N+ doped Si wafer base 1006. Photodiodes 1002, 1004 have respective contact pads 1008, 1010. Above the photodiodes 1002, 1004 (hence opposite base 1006) and directly coupled thereto is a single, cylindrical, high Z scintillator 1012 (of, for example, CsI(Tl) or YLSO).

It should also be noted that DPSS detector module 1000 is designed to be oriented, in use, with Si base 1006 directed towards the radiation source, and with scintillator 1012 directed away from the radiation source. In order to separate low energy photoelectric effect events originated in a inner Si photodiode 1002 from the Compton background of any masking isotopes, DPSS detector module 1000 includes a light reflecting medium between the sensitive part of inner photodiode 1002 and the scintillator 1012, in this embodiment in the form of an aluminium film 1102 (see FIGS. 11A and 11B) of 0.5-1 micron thickness on the upper surface of inner photodiode 1002 (shown hashed, including covering the contact pad of the inner photodiode 1002). Al film 1102 acts as a mirror to prevent inner photodiode 1002 from detecting photons (of essentially optical wavelengths) arising from events in scintillator 1014. The low energy gamma or X-ray photons of interest—if forward scattered in inner photodiode 1002 towards scintillator 1012—are not impeded by Al film 1102. In alternative embodiments the same objective can be accomplished by locating an opaque, light Z material under the scintillator 1012 (such as in a recess in the underside of scintillator 1012), or by coating the underside of scintillator 1012 (or a recess therein) with reflective paint or the like.

Figure 11A:
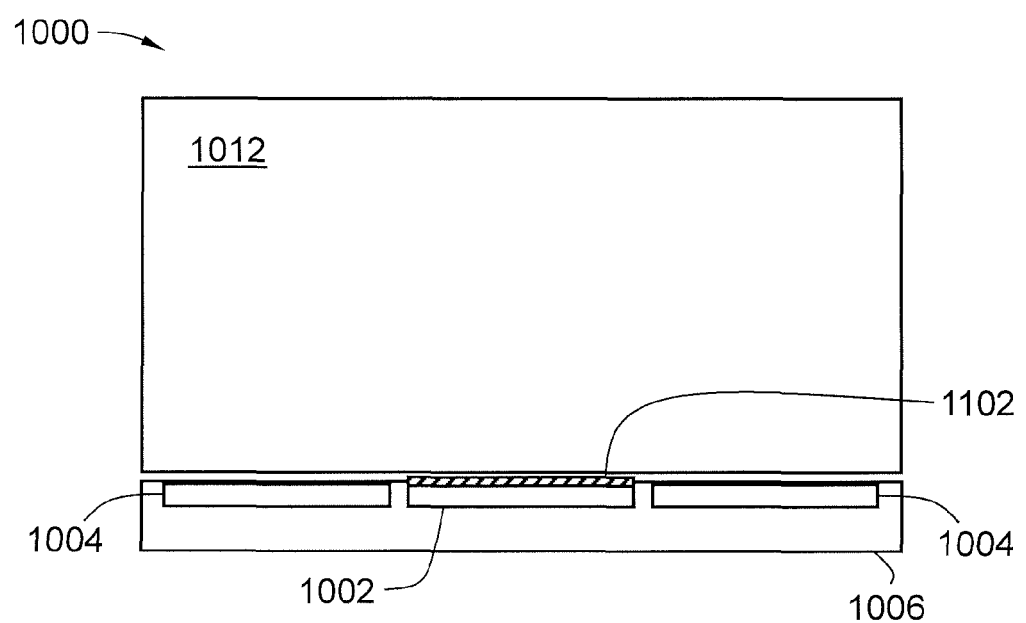
FIG. 11A is a schematic cross sectional view of the detector module of FIG. 10.
Figure 11B:
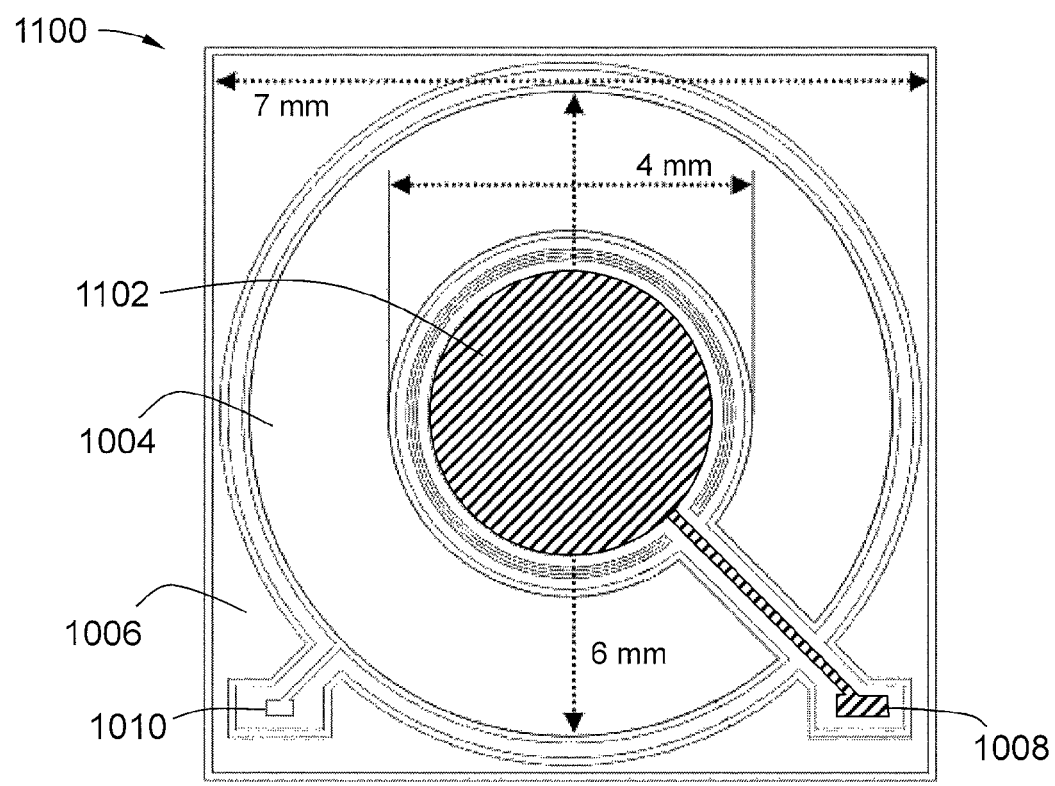
FIG. 11B is a plan view of the inner and outer photodiodes on a single Si substrate (base) and Al film of the detector module of FIG. 10.

FIG. 11A is a schematic cross sectional view of DPSS detector module 1000, showing inner and outer photodiodes 1002, 1004, Si base 1006, scintillator 1012 and Al film 1102. FIG. 11B is a plan view, in which inner photodiode 1002 is concealed under Al film 1102, but outer photodiode 1004 and Si base 1006 are visible; typical dimensions are indicated. It will be noted that DPSS detector module 1000 is comparable in overall size to DPDS detector module 100 of FIG. 1.

Thus, low energy gamma photons and X-rays—entering the detector module 1000 from below in the view of FIGS. 10 and 11A—interact in the inner photodiode 1002 and are outputted as a first channel. Compton events in inner photodiode 1002, if forward scattered towards scintillator 1012, are absorbed by scintillator 1012 but—as explained above—can be detected only by outer photodiode 1004 owing to Al film 1102, hence as a second channel. Thus, Compton suppression can be effected (such as by deploying detector module 1000 in a spectrometer comparable to spectrometer 700 of FIG. 7). Photons that are backscattered from the inner photodiode 1002 produce high energy electrons that may be scattered into scintillator 1012; this also produces a signal in outer photodiode 1004 and hence the second channel. The efficiency of detector module 1000 depends on the Z and thickness of scintillator 1012. It has been shown that detector module 1000 has minimal cross-talk between inner and outer photodiodes 1002, 1004, which protects inner photodiode 1002 (or channel 1) from "direct events" in outer photodiode 1004 (or channel 2). Further, Compton scattering events in outer photodiode 1004 that cause a Compton electron to deposit energy in both the inner and outer photodiodes 1002, 1004 can clearly be readily rejected using the anti-Compton mode of spectrometer 700 of FIG. 7, as described above.

The DPSS detector module 1000 thus extends the energy range of gamma photon spectroscopy. Outer photodiode 1004 and scintillator 1012 (channel 2) can be used as would a standard scintillator detector, with good efficiency for high energy photons, and possibly for gamma ray spectroscopy for photon energies of more than 80-90 keV and in standard conditions. The inner 0.5 mm thickness Si photodiode with the rejection mode described above makes detector module 1000 suitable for gamma spectroscopy at photon energies of about 10 to 100 keV. A wide photon energy range can thus be detected in a compact device (including of portable size), and spectra can be presented in the same scale using scaling from both channels. The small area of the inner photodiode 1002 contributes to good spatial resolution.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in Australia or any other country.

The invention claimed is:

1. A radiation detection apparatus, comprising: a first scintillator for interacting with radiation and outputting light in response thereto the first scintillator having a front surface, a rear surface and an external peripheral surface therebetween;
   a first photodetector adjacent to and coextensive with said rear surface of said first scintillator, for receiving and detecting light from said first scintillator and outputting a first output signal in response thereto;
   a second scintillator located around said peripheral surface of said first scintillator, for interacting with radiation and outputting light in response thereto, said second scintillator having a front surface and a rear surface; and
   a second photodetector adjacent to and coextensive with said rear surface of said second scintillator for receiving and detecting light from said second scintillator and outputting a second output signal in response thereto.

2. An apparatus as claimed in claim 1, wherein each of said first and second scintillators is cylindrical and integral, and said first and second scintillators are coaxial.

3. An apparatus as claimed in claim 1, wherein said apparatus has a principal output comprising or derived from said first output signal, and said second output signal is used to increase total detection efficiency of said apparatus.

4. An apparatus as claimed in claim 1, wherein said second scintillator extends away from said, first and second photodetectors beyond said first scintillator, such that said rear surfaces of said first and second scintillators are coplanar and said front surface of said second scintillator is forward of said front surface of said first scintillator.

5. An apparatus as claimed in claim 1, including an optical isolator located between said first and second scintillators, surrounding said peripheral surface of said first scintillator and extending from said rear surface to said front surface of said first scintillator.

6. An apparatus as claimed in claim 1, wherein each of said first and second photodetectors is continuous, and said first and second photodetectors are coplanar and concentric.

7. An apparatus as claimed in claim 1, wherein said first and second photodetectors are on a single substrate and produced on said substrate.

8. An apparatus as claimed in claim 1, including anticoincidence electronics arranged to receive said first output signal and said second output signal, and to output a signal corresponding to said first output signal when said first output signal is not in coincidence with said second output signal.

9. An apparatus as claimed in claim 1, wherein said second scintillator has an external peripheral surface between said front surface and said rear surface of said second scintillator, and said apparatus further comprises:
a third scintillator for interacting with radiation and outputting light in response thereto, said third scintillator having a front surface and a rear surface and being located around said peripheral surface of said second scintillator; and
a third photodetector adjacent to and coextensive with said rear surface of said third scintillator for receiving and detecting light from said third scintillator and outputting a third output signal in response thereto.

10. An apparatus as claimed in claim 1, wherein said apparatus is adapted to act as a beta detection apparatus.

11. An apparatus as claimed in claim 10, including shielding located around exposed portions of said second scintillator to prevent beta particles from interacting with said second scintillator, wherein said apparatus is configured to output a measure of counts attributable to beta particles by outputting the second output signal suitably normalized subtracted from the first output signal.

12. An apparatus as claimed in claim 1, wherein said first photodetector comprises a plurality of adjacent photodetector elements for receiving and detecting light; from said first scintillator and outputting respective output signals in response thereto.

13. An apparatus as claimed in claim 1, wherein said first scintillator comprises a plurality of coaxial scintillator elements and said first photodetector comprises a plurality of photodetector elements, each of said photodetector elements being adjacent to and coextensive with a respective one of said scintillator elements and arranged to receive and detect light from said respective scintillator element and to output a respective output signal in response thereto.

14. An apparatus as claimed in claim 13, including optical isolator located between said respective scintillator elements.

15. An apparatus as claimed in claim 1, wherein said second photodetector comprises a plurality of photodetector elements for receiving and detecting light from said second scintillator and outputting respective output signals in response thereto.

16. An apparatus as claimed in claim 1, wherein said second scintillator comprises a plurality of coaxial scintillator elements and said second photodetector comprises a plurality of photodetector elements, each of said photodetector elements being adjacent to and coextensive with a respective one of said scintillator elements and arranged to receive and detect light from said respective scintillator element and to output a respective output signal in response thereto.

17. An apparatus as claimed in claim 16, including optical isolator located between said respective scintillator elements.

18. An apparatus as claimed in claim 1, wherein said second scintillator has an external peripheral surface between said front surface and said rear surface of said second scintillator, and said apparatus further comprises:
a plurality of further scintillators for interacting with radiation and outputting light in response thereto, each of said further scintillators having respective front surfaces and rear surfaces; and
a plurality of further photodetectors, each adjacent to and coextensive with a respective one of said rear surfaces of said further scintillators, for receiving and detecting light from said respective further scintillator and outputting a respective output signal in response thereto;
wherein said second scintillator and said plurality of further scintillators are nested coaxially around said first scintillator.

19. An apparatus as claimed in claim 1, wherein said first and second photodetectors are on a single substrate.

20. An apparatus as claimed in claim 1, wherein said first and second photodetectors are on a single substrate that comprises an N+ doped silicon wafer.

21. An apparatus as claimed in claim 1, wherein:
said second scintillator extends away from said first and second photodetectors beyond said first scintillator, such that said rear surfaces of said first and second scintillators are coplanar and said front surface of said second scintillator is forward of said front surface of said first scintillator;
said apparatus further comprises shielding located around exposed portions of said second scintillator to prevent beta particles from interacting with said second scintillator; and
said apparatus is configured to output a measure of counts attributable to beta particles by outputting the second output signal suitably normalized subtracted from the first output signal whereby said apparatus is adapted to act as a beta detection apparatus.

22. A method of measuring or monitoring radiation, comprising: receiving radiation with a first1 scintillator having a front surface, a rear surface and an external peripheral surface therebetween;
detecting light output by said first scintillator with a first photodetector located adjacent to and coextensive with said rear surface of said first scintillator;
outputting a first output signal, from said first photodetector in response to light detected by said first photodetector;
receiving radiation with a second scintillator located around said peripheral surface of said first scintillator, said second scintillator having a front surface and a rear surface;
detecting light output by said second scintillator with a second photodetector located adjacent to and coextensive with said rear surface of said second scintillator; and
outputting a second output signal from said second photodetector in response to light detected by said second photodetector.

23. A method as claimed in claim 22, including generating a principal output comprising or derived from said first output signal, and total detection efficiency with said second output signal.

24. A method as claimed in claim 22, including optically isolating said first and second scintillators with an optical isolator located between said first and second scintillators, surrounding said peripheral surface of said first scintillator and extending from said rear surface to said front surface of said first scintillator.

25. A method as claimed in claim 22, including providing said first and second photodetectors on a single substrate.

26. A method as claimed in claim 22, wherein said first and second scintillators are cylindrical and coaxial.

* * * * *

UNITED STATES PATENT AND TRADEMARK OFFICE
CERTIFICATE OF CORRECTION

PATENT NO. : 8,212,220 B2  
APPLICATION NO. : 12/526100  
DATED : July 3, 2012  
INVENTOR(S) : Michael Lloyd Franz Lerch It is certified that error appears in the above-identified patent and that said Letters Patent is hereby corrected as shown below:

Cover Page, Col. 1, line 2, for Assignee, Delete "(GB)" and insert -- (AU) --, therefor.

Col. 13, line 14, in Claim 9, delete "scintillator" and insert -- scintillator, --, therefor.

Col. 14, line 31, in Claim 22, delete "first1" and insert -- first --, therefor.

Col. 14, line 52, in Claim 23, delete "and total" and insert -- and increasing total --, therefor.

Signed and Sealed this  
Ninth Day of October, 2012

David J. Kappos  
*Director of the United States Patent and Trademark Office*